United States Patent
Datta et al.

(10) Patent No.: US 9,376,419 B2
(45) Date of Patent: Jun. 28, 2016

(54) SOLID FORMS OF NILOTINIB HYDROCHLORIDE

(71) Applicant: APOTEX INC., Toronto (CA)

(72) Inventors: Probal Kanti Datta, Hamilton (CA);
Carlos Zetina-Rocha, Burnaby (CA);
Cameron L. McPhail, Brantford (CA);
Yajun Zhao, Brantford (CA); Gamini Weeratunga, Ancaster (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 14/436,049

(22) PCT Filed: Oct. 15, 2013

(86) PCT No.: PCT/CA2013/000863
§ 371 (c)(1),
(2) Date: Apr. 15, 2015

(87) PCT Pub. No.: WO2014/059518
PCT Pub. Date: Apr. 24, 2014

(65) Prior Publication Data
US 2015/0274699 A1    Oct. 1, 2015

Related U.S. Application Data

(60) Provisional application No. 61/714,120, filed on Oct. 15, 2012.

(51) Int. Cl.
*C07D 401/14*    (2006.01)

(52) U.S. Cl.
CPC ........... *C07D 401/14* (2013.01); *C07B 2200/13* (2013.01)

(58) Field of Classification Search
CPC .......................... C07D 401/14; C07B 2200/13
See application file for complete search history.

(56) References Cited

U.S. PATENT DOCUMENTS

| | | |
|---|---|---|
| 2008/0269269 A1 | 10/2008 | Manley et al. |
| 2010/0190812 A1 | 7/2010 | Sterimbaum et al. |
| 2013/0210847 A1 | 8/2013 | Kompella et al. |

FOREIGN PATENT DOCUMENTS

| | | |
|---|---|---|
| CN | 102453024 A | 5/2012 |
| IN | 3577CHE2010 A | 7/2012 |
| WO | 2007015871 A1 | 2/2007 |
| WO | 2010009402 A2 | 1/2010 |
| WO | 2011033307 A1 | 3/2011 |
| WO | 2011086541 A1 | 7/2011 |
| WO | 2011163222 A1 | 12/2011 |
| WO | 2012055351 A1 | 5/2012 |
| WO | 2012070062 A2 | 5/2012 |
| WO | 2014174456 A2 | 10/2014 |

OTHER PUBLICATIONS ip.com Journal (2009) 9(9B), 61 "NLT HCl Crystalline Forms" (IPCOM000187328D) Sep. 2, 2009.
ip.com Journal (2009) 9(12B), 14 "NLT HCl Crystalline Forms" (IPCOM000190565D) Dec. 6, 2009 1-25 Dec. 6, 2009.
ip.com Journal (2010) 10(3B), 11 "Crystalline Forms of NLT HCL" 1-25 (IPCOM000193749D) Mar. 8, 2010.
ip.com Journal (2010) 10(5A), 25 "Crystalline Form of 4-methyl-N-[3-(4-methyl-1H-imidazol-1-yl)-5- (trifluoromethyl)phenyl]-3-[[4-(3-pyridinyl)-2-pyrimidinyl]amino]-benzamide" (IPCOM000195326D) Apr. 29, 2010.
ip.com Journal (2010) 10(9A), 21 "Crystalline forms of 4-methyl-N-[3-(4-methyl-1H-imidazol-1-yl)-5- (trifluoromethyl)phenyl]-3-[[4-(3-pyridinyl)-2-pyrimidinyl]amino]- benzamide salts" (IPCOM000199113D) Aug. 26, 2010.
ip.com Journal (2010) 10(12A), 18 "Crystalline forms of 4-methyl-N-[3-(4-methyl-1H-imidazol-1-yl)-5- (trifluoromethyl)phenyl]-3-[[4-(3-pyridinyl)-2-pyrimidinyl]amino]- benzamide salts" (IPCOM000201702D) Nov. 18, 2010.
ip.com Journal (2010) 10(12B), 28 "A crystallization process for 4-methyl-N-[3-(4-methyl-1H-imidazol-1-yl)-5-(trifluoromethyl)phenyl]-3-[[4-(3-pyridiny1)-2-pyrimidinyl]amino]-benzamide" (IPCOM000202210D) Dec. 9, 2010.
ip.com Journal (2010) 10(7B), 3 "Amorphous 4-methyl-N-[3-(4-methyl-1H-imidazol-1-yl)-5-(trifluoromethyl)phenyl]-3-[[4-(3-pyridinyl)-2-pyrimidinyl]amino]-benzamide salts" (IPCOM000197295D) Jul. 1, 2010.
ip.com Journal (2009), "NLT HCl Crystalline Forms" (IPCOM000183524D) May 26, 2009.

*Primary Examiner* — Samantha Shterengarts
*Assistant Examiner* — Matt Mauro
(74) *Attorney, Agent, or Firm* — The Webb Law Firm

(57) ABSTRACT

Disclosed are solid forms of Nilotinib hydrochloride and methods of preparation of various crystalline solvates of Nilotinib HCl including benzyl alcohol, acetic acid, propylene glycol, and isopropanol. Nilotinib HCl is a tyrosine kinase inhibitor used for the treatment of drug resistant chronic myelogenous leukemia (CML).

18 Claims, 7 Drawing Sheets

SOLID FORMS OF NILOTINIB HYDROCHLORIDE

TECHNICAL FIELD

The present invention is directed to solid forms of Nilotinib hydrochloride and methods for the preparation thereof.

BACKGROUND

Nilotinib hydrochloride (1) is a tyrosine kinase inhibitor used for the treatment of drug-resistant chronic myelogenous leukemia (CML). It is marketed in the United States as Tasigna™.

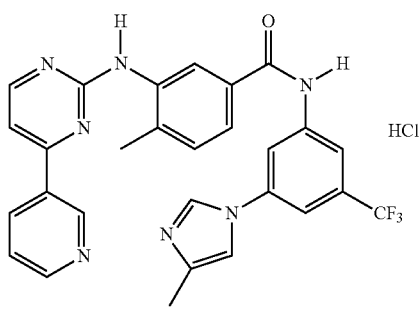

US20080269269 discloses preparation of polymorphic forms of 4-methyl-N-[3-(4-methylimidazol-1-yl)-5-trifluoromethyl-phenyl)3-(4-pyridin-3-yl-pyrimidin-2-ylamino)-benzamide free base and salts thereof by various processes.

US20100190812 discloses crystalline forms of Nilotinib hydrochloride.

WO2011/086541 relates to a novel polymorph of 4-methyl-N-[3-(4-methylimidazol-1-yl)-5-(trifluoromethyl)-phenyl]-3-[(4-pyridin-3-yl-pyrimidin-2-yl)amino]benzamide (Nilotinib) monohydrochloride monohydrate, and to methods for preparing, pharmaceutical compositions comprising, and methods of treatment using said polymorph.

Crystalline Forms of NLT HCl are disclosed in IP.com Journal (2010), 10(3B), 11; IP.com Journal (2009), 9(12B), 14; IP.com Journal (2009), 9(9B), 61; and IP.com PriorArt DataBase.IP.com Number (May 26, 2009) IPCOM000183524D.

IP.com Journal (2010), 10(5A), 25 discloses a crystalline form of 4-methyl-N-[3-(4-methyl-1H-imidazol-1-yl)-5-(trifluoromethyl)phenyl]-3-[[4-(3-pyridinyl)-2-pyrimdinyl]amino]-benzamide.

IP.com Journal (2010), 10(12A), 18 and IP.com Journal (2010), 10(9A), 21 discloses crystalline forms of 4-methyl-N-[3-(4-methyl-1H-imidazol-1-yl)-5-(trifluoromethyl)phenyl]-3-[[4-(3-pyridinyl)-2-pyrimidinyl]amino]-benzamide salts.

IP.com Journal (2010), 10(12B), 28 discloses a crystallization process for 4-methyl-N-[3-(4-methyl-1H-imidazol-1-yl)-5-(trifluoromethyl)phenyl]-3-[[4-(3-pyridinyl)-2-pyrimidinyl]amino]-benzamide.

IP.com Journal (2010), 10(7B), 3 discloses amorphous 4-methyl-N-[3-(4-methyl-1H-imidazol-1-yl)-5-(trifluoromethyl)phenyl]-3-[[4-(3-pyridinyl)-2-pyrimidinyl]amino]-benzamide salts.

WO2011163222 discloses Nilotinib salts and crystalline forms thereof.

WO2012055351 discloses a crystal form of Nilotinib hydrochloride with X-ray powder diffraction as disclosed in Table 1 and a preparation method thereof.

WO2012070062 discloses a novel crystalline form of Nilotinib hydrochloride, process for its preparation and pharmaceutical compositions comprising it.

SUMMARY

The present invention relates to solid forms of Nilotinib hydrochloride and methods for the preparation thereof. The Nilotinib forms of the present invention may exhibit improved physical stability compared to known forms, particularly known solvated forms such as methanol solvates. Some methanol solvates, such as some of those set out in US20080269269, undergo conversion to hydrate forms upon exposure to ambient conditions. The forms of the present invention may exhibit good stability in ambient conditions and may not readily convert to hydrated forms. Forms of the present invention may have low toxicity and may not incorporate solvents such as methanol and dimethylformamide which, according to ICH guidelines, should be limited in pharmaceutical products because of their inherent toxicity.

In illustrative embodiments, there is provided a crystalline solid form of Nilotinib hydrochloride having an X-ray powder diffraction pattern comprising peaks, in terms of degrees 2-theta, at approximately 6.0, 6.5, 18.1, 19.5, 20.8 and 25.3.

In illustrative embodiments, there is provided a crystalline solid form of Nilotinib hydrochloride described herein having an X-ray powder diffraction pattern substantially similar to the X-ray powder diffraction pattern as shown in FIG. 1.

In illustrative embodiments, there is provided a crystalline solid form of Nilotinib hydrochloride described herein having an X-ray powder diffraction pattern as shown in FIG. 1.

In illustrative embodiments, there is provided a crystalline solid form of Nilotinib hydrochloride described herein wherein the crystalline solid form of Nilotinib hydrochloride is a benzyl alcohol solvate wherein the molar ratio of Nilotinib hydrochloride to benzyl alcohol is approximately 1:1.

In illustrative embodiments, there is provided a crystalline solid form of Nilotinib hydrochloride having an X-ray powder diffraction pattern comprising peaks, in terms of degrees 2-theta, at approximately 7.5, 9.1, 11.0, 19.6, 20.8, 21.8, and 24.1.

In illustrative embodiments, there is provided a crystalline solid form of Nilotinib hydrochloride described herein having an X-ray powder diffraction pattern similar to the X-ray powder diffraction pattern as shown in FIG. 2.

In illustrative embodiments, there is provided a crystalline solid form of Nilotinib hydrochloride described herein having an X-ray powder diffraction pattern as shown in FIG. 2.

In illustrative embodiments, there is provided a crystalline solid form of Nilotinib hydrochloride described herein having a differential scanning calorimetry thermogram comprising an endothermic peak with an onset temperature of approximately 134° C.

In illustrative embodiments, there is provided a crystalline solid form of Nilotinib hydrochloride described herein having a differential scanning calorimetry thermogram substantially similar to the differential scanning calorimetry thermogram as shown in FIG. 3.

In illustrative embodiments, there is provided a crystalline solid form of Nilotinib hydrochloride described herein having a differential scanning calorimetry thermogram as shown in FIG. 3.

In illustrative embodiments, there is provided a crystalline solid form of Nilotinib hydrochloride described herein wherein the crystalline solid form of Nilotinib hydrochloride is a propylene glycol solvate wherein the molar ratio of propylene glycol to Nilotinib hydrochloride is approximately 1:1.

In illustrative embodiments, there is provided a crystalline solid form of Nilotinib hydrochloride having an X-ray powder diffraction pattern comprising peaks, in terms of degrees 2-theta, at approximately 6.2, 12.5, 18.8, 22.0, 24.0, and 26.0.

In illustrative embodiments, there is provided a crystalline solid form of Nilotinib hydrochloride described herein having an X-ray powder diffraction pattern substantially similar to the X-ray powder diffraction pattern as shown in FIG. 4.

In illustrative embodiments, there is provided a crystalline solid form of Nilotinib hydrochloride described herein having an X-ray powder diffraction pattern as shown in FIG. 4.

In illustrative embodiments, there is provided a crystalline solid form of Nilotinib hydrochloride described herein wherein crystalline solid form of Nilotinib hydrochloride comprises acetic acid salt wherein the molar ratio of acetic acid to Nilotinib hydrochloride is approximately 2:1.

In illustrative embodiments, there is provided a crystalline solid form of Nilotinib hydrochloride having an X-ray powder diffraction pattern comprising peaks, in terms of degrees 2-theta, at approximately 6.8, 9.2, 13.1, 13.9, 17.9 and 25.3.

In illustrative embodiments, there is provided a crystalline solid form of Nilotinib hydrochloride described herein having an X-ray powder diffraction pattern substantially similar to the X-ray powder diffraction pattern as shown in FIG. 5.

In illustrative embodiments, there is provided a crystalline solid form of Nilotinib hydrochloride described herein having an X-ray powder diffraction pattern as shown in FIG. 5.

In illustrative embodiments, there is provided a crystalline solid form of Nilotinib hydrochloride described herein having a differential scanning calorimetry thermogram comprising an endothermic peak with an onset temperature of approximately 210° C.

In illustrative embodiments, there is provided a crystalline solid form of Nilotinib hydrochloride described herein having a differential scanning calorimetry thermogram substantially similar to the differential scanning calorimetry thermogram as shown in FIG. 6.

In illustrative embodiments, there is provided a crystalline solid form of Nilotinib hydrochloride described herein having a differential scanning calorimetry thermogram as shown in FIG. 6.

In illustrative embodiments, there is provided a crystalline solid form of Nilotinib hydrochloride having an X-ray powder diffraction pattern comprising peaks, in terms of degrees 2-theta, at approximately 7.2, 9.6, 16.0, 17.6, 21.8, and 26.0.

In illustrative embodiments, there is provided a crystalline solid form of Nilotinib hydrochloride described herein having an X-ray powder diffraction pattern substantially similar to the X-ray powder diffraction pattern as shown in FIG. 7.

In illustrative embodiments, there is provided a crystalline solid form of Nilotinib hydrochloride described herein having an X-ray powder diffraction pattern as shown in FIG. 7.

In illustrative embodiments, there is provided a crystalline solid form of Nilotinib hydrochloride described herein wherein the crystalline solid form of Nilotinib hydrochloride comprises acetic acid salt wherein the molar ratio of acetic acid to Nilotinib hydrochloride is approximately 1:1.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
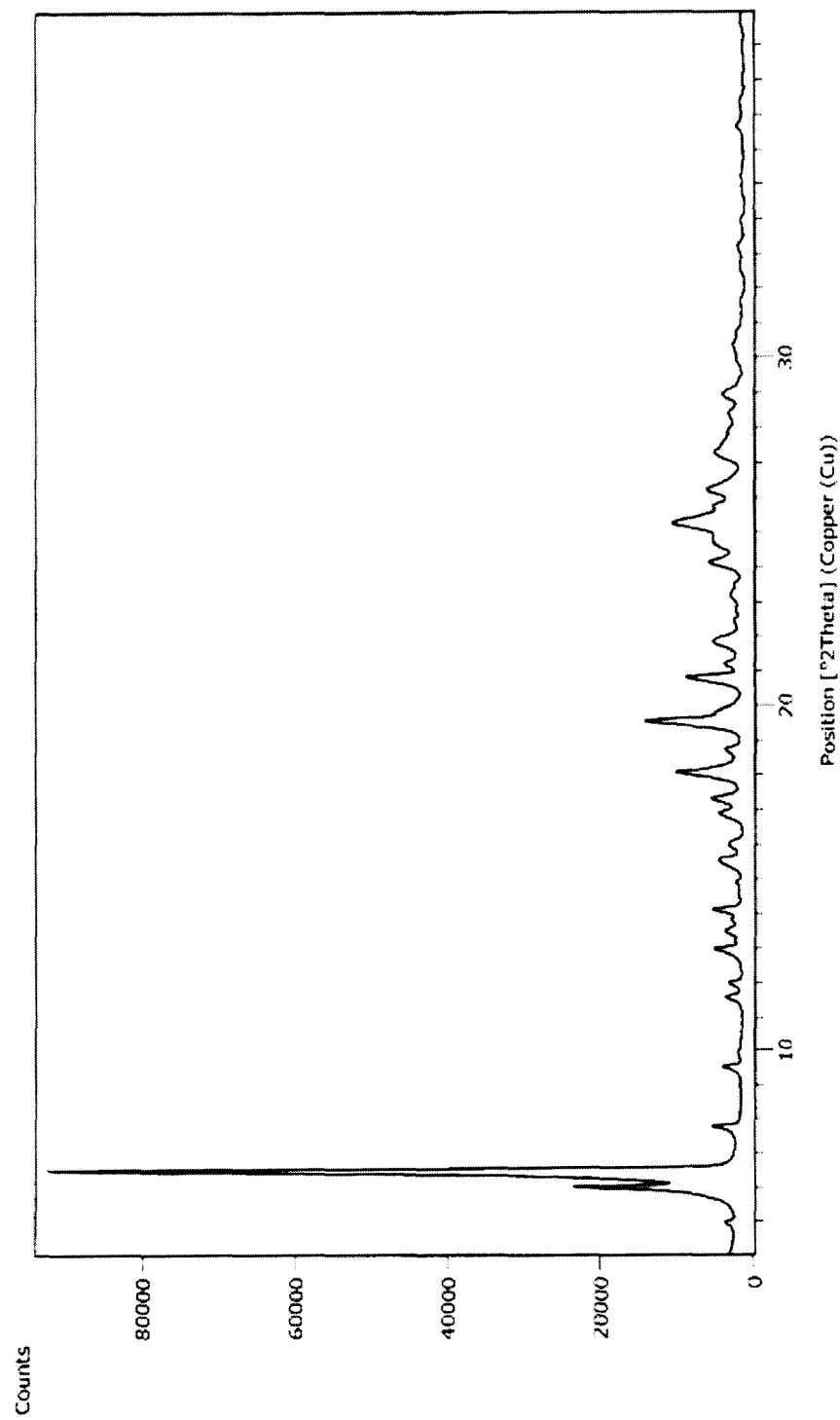
FIG. 1 is a Powder X-Ray Diffractogram (PXRD) of solid form APO-I of Nilotinib hydrochloride as prepared in Example 1.

When used in reference to a diffractogram, a spectrum and/or data presented in a graph, the term "substantially similar" means that the subject diffractogram, spectrum and/or data presented in a graph encompasses all diffractograms, spectra and/or data presented in graphs that vary within acceptable boundaries of experimentation that are known to a person of skill in the art. Such boundaries of experimentation will vary depending on the type of the subject diffractogram, spectrum and/or data presented in a graph, but will nevertheless be known to a person of skill in the art.

When used in reference to a peak in an X-ray powder diffraction pattern (PXRD) diffractogram, the term "approximately" means that the peak may vary by ±0.2 degrees 2-theta of the subject value.

When used in reference to a peak in a DSC thermogram, the term "approximately" means that the peak may vary by ±1° C. of the subject value.

As used herein when referring to a diffractogram, spectrum and/or to data presented in a graph, the term "peak" refers to a feature that one skilled in the art would recognize as not attributable to background noise.

Depending on the nature of the methodology applied and the scale selected to display results obtained from an X-ray diffraction analysis, an intensity of a peak obtained may vary quite dramatically. For example, it is possible to obtain a relative peak intensity of 1% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

As used herein, the term 'solid form' or 'form' refers to a substance with a particular arrangement of components in the crystal lattice, and which may be identified by physical characterization methods such as PXRD. As used herein, the term solid form is intended to include single-component and multiple-component forms of Nilotinib hydrochloride. Single-component forms of Nilotinib hydrochloride consist solely of Nilotinib hydrochloride in the crystal lattice. Multiple-component forms of Nilotinib hydrochloride include solvates, hydrates and salts of Nilotinib hydrochloride wherein the solvent, water or counterion, respectively, are also incorporated into the crystal lattice. In both single-component and multiple-component forms, there can exist more than one three-dimensional arrangement of components in the crystal lattice, which may give rise to differences in physical properties and which can be detected by physical characterization methods, such as PXRD. Where the exact nature of a multiple-component system (solvate or salt, for example) is not explicitly stated, the form shall be identified by the physical characterization data such as PXRD.

In an illustrative embodiment, the present invention comprises a crystalline solid form of Nilotinib hydrochloride which is referred to herein as APO-I. APO-I may be characterized by an X-ray powder diffraction pattern comprising peaks, in terms of degrees 2-theta, at approximately 6.0±0.2, 6.5±0.2, 18.1±0.2, 19.5±0.2, 20.8±0.2 and 25.3±0.2. An illustrative PXRD diffractogram of APO-I is given in FIG. 1.

APO-I may have a reflection ("peak") at any one or more of the values expressed in degrees 2-theta given in Table 1. Although values are given in the tables below, APO-I may be defined by the claimed peaks and a particular claim may be limited to one peak only, or several peaks. The form APO-I does not have to include all or even many of the peaks listed in Table 1. Some illustrative and non-limiting possible observations regarding relative intensities of the peaks are set out in Table 1.

TABLE 1

Relative peak intensities for APO-I

| Angle 2-theta | Relative intensity % |
|---|---|
| 5.99 | 22.01 |
| 6.48 | 100.00 |
| 7.74 | 4.48 |
| 9.51 | 3.14 |
| 12.95 | 4.44 |
| 14.11 | 4.96 |
| 15.49 | 4.08 |
| 16.88 | 3.83 |
| 17.30 | 4.62 |
| 18.06 | 11.14 |
| 19.52 | 16.81 |
| 20.76 | 8.97 |
| 21.83 | 4.85 |
| 24.12 | 5.70 |
| 25.25 | 11.88 |
| 26.25 | 5.12 |

Form APO-I may be prepared by treating Nilotinib free base with hydrogen chloride in a solvent consisting of benzyl alcohol to provide a mixture. Often, the amount of benzyl alcohol may vary from about 4 volumes to about 10 volumes. The mixture may be stirred for a suitable period of time to allow formation of form APO-I. Often, the mixture is stirred from about 15 hours to about 24 hours before isolation of form APO-I. Following isolation, the solid may be dried at ambient pressure or in vacuo from about 20° C. to about 60° C. The time required for drying will depend on the conditions and may vary from about 15 hours to about 3 days. Often, the solid is dried for about 24 hours in vacuo.

In an illustrative embodiment, the present invention comprises a crystalline solid form of Nilotinib hydrochloride which is referred to herein as APO-II. APO-II may be characterized by an X-ray powder diffraction pattern comprising peaks, in terms of degrees 2-theta, at approximately 7.5±0.2, 9.1±0.2, 11.0±0.2, 19.6±0.2, 20.8±0.2, 21.8±0.2, and 24.1±0.2. An illustrative PXRD diffractogram of APO-II is given in FIG. 2.

APO-II may have a reflection ("peak") at any one or more of the values expressed in degrees 2-theta given in Table 2. Although values are given in the tables below, APO-II may be defined by the claimed peaks and a particular claim may be limited to one peak only, or several peaks. The form APO-II does not have to include all or even many of the peaks listed in Table 2. Some illustrative and non-limiting possible observations regarding relative intensities of the peaks are set out in Table 2.

TABLE 2

Relative peak intensities for APO-II

| Angle 2-theta | Relative intensity % |
|---|---|
| 7.46 | 100.00 |
| 9.08 | 79.63 |
| 10.99 | 34.05 |
| 12.34 | 9.67 |
| 13.30 | 4.93 |
| 13.86 | 2.64 |
| 14.84 | 31.72 |
| 15.08 | 17.81 |
| 15.94 | 24.78 |
| 17.09 | 15.16 |
| 18.31 | 9.65 |
| 19.60 | 44.19 |
| 20.82 | 34.75 |
| 21.77 | 34.88 |
| 22.62 | 12.28 |
| 24.08 | 47.32 |
| 24.67 | 13.21 |
| 25.25 | 43.37 |
| 25.75 | 16.34 |
| 26.67 | 35.00 |
| 28.33 | 14.78 |

Figure 3:
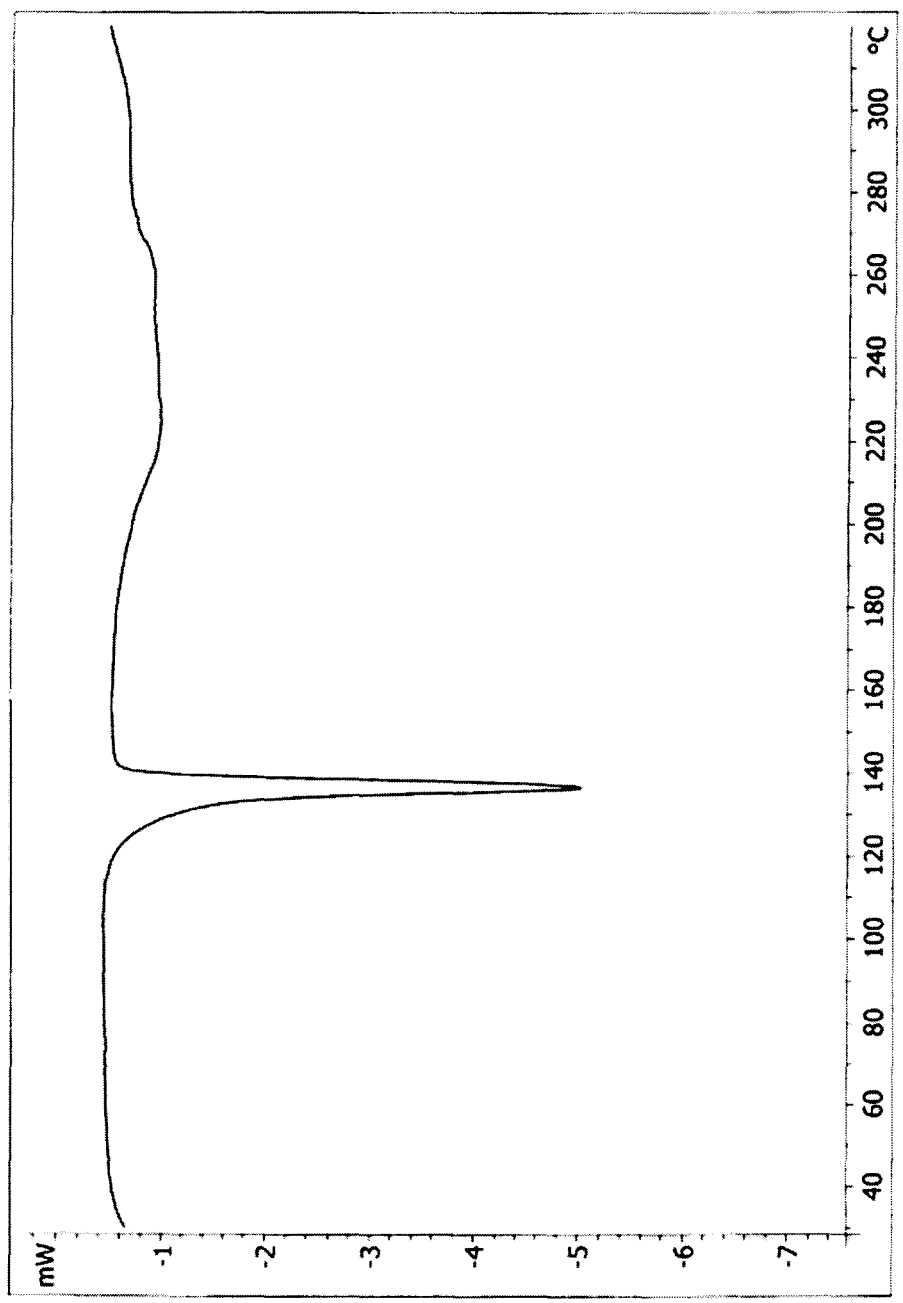
FIG. 3 is a Differential Scanning calorimetry (DSC) thermogram of solid form APO-II of Nilotinib hydrochloride as prepared in Example 2.

An illustrative DSC thermogram of form APO-II is shown in FIG. 3. The DSC thermogram shown in FIG. 3 may be illustrative of the type of results obtained when analysing form APO-II by DSC. The DSC thermogram may be further characterized by a peak endotherm with an onset temperature of approximately 134° C. and a peak maximum of approximately 136° C.

Form APO-II may be prepared by treating Nilotinib free base with hydrogen chloride in a solvent consisting of a mixture of 1,2-propanediol and methanol to provide a mixture. The amount of 1,2-propanediol may vary, with higher amounts resulting in increased drying times. Often a minimum amount of about 2 molar equivalents with respect to Nilotinib is used. The amount of methanol may vary wherein a minimum of about 4 volumes with respect to Nilotinib is often used. The mixture may be stirred for a suitable period of time to allow formation of form APO-II. Often, the mixture is stirred for from about 6 to about 12 hours before isolation of form APO-II. Form APO-II may be isolated by gradual evaporation of the bulk of the solvent. Following isolation, the form APO-II may be dried at ambient pressure or in vacuo at a temperature of from about 20° C. to about 50° C. The drying time may vary depending on the conditions, with a minimum of about 12 hours often employed.

In an illustrative embodiment, the present invention comprises a crystalline solid form of Nilotinib hydrochloride which is referred to herein as APO-III. APO-III may be characterized by an X-ray powder diffraction pattern comprising peaks, in terms of degrees 2-theta, at approximately 6.2±0.2, 12.5±0.2, 18.8±0.2, 22.0±0.2, 24.0±0.2, and 26.0±0.2. An illustrative PXRD diffractogram of APO-III is given in FIG. 4.

APO-III may have a reflection ("peak") at any one or more of the values expressed in degrees 2-theta given in Table 3. Although values are given in the tables below, APO-III may be defined by the claimed peaks and a particular claim may be limited to one peak only, or several peaks. The form APO-III does not have to include all or even many of the peaks listed in Table 3. Some illustrative and non-limiting possible observations regarding relative intensities of the peaks are set out in Table 3.

TABLE 3

Relative peak intensities for APO-III

| Angle 2-theta | Relative intensity % |
|---|---|
| 6.20 | 100.00 |
| 10.01 | 9.54 |
| 11.21 | 12.17 |
| 12.48 | 15.36 |
| 14.00 | 7.98 |
| 14.33 | 14.76 |
| 14.54 | 14.16 |
| 15.37 | 18.64 |
| 16.08 | 22.14 |
| 18.80 | 29.64 |
| 21.59 | 12.68 |
| 21.97 | 18.09 |
| 23.98 | 45.79 |
| 25.27 | 13.53 |
| 26.02 | 50.72 |
| 26.36 | 17.35 |
| 27.83 | 13.59 |

Form APO-III may be prepared by treating a solution of Nilotinib free base in acetic acid with hydrogen chloride to provide a mixture. The amount of acetic acid with respect to Nilotinib may vary from a minimum of about 3 volumes. The mixture may be stirred for a suitable period of time at a suitable temperature to allow formation of form APO-Ill. Often, the mixture is stirred at a temperature of from about 35° C. to about 50° C. for a minimum of about 12 hours before isolation of form APO-Ill. Following isolation, form APO-III may be dried at ambient pressure or in vacuo at a temperature of from about 20° C. to about 60° C. The drying time may vary depending on the conditions, with a minimum of about 12 hours often employed.

In an illustrative embodiment, the present invention comprises a crystalline solid form of Nilotinib hydrochloride which is referred to herein as APO-IV. APO-IV may be characterized by an X-ray powder diffraction pattern comprising peaks, in terms of degrees 2-theta, at approximately 6.8±0.2, 9.2±0.2, 13.1±0.2, 13.9±0.2, 17.9±0.2 and 25.3±0.2. An illustrative PXRD diffractogram of APO-IV is given in FIG. 5.

APO-IV may have a reflection ("peak") at any one or more of the values expressed in degrees 2-theta given in Table 4. Although values are given in the tables below, APO-IV may be defined by the claimed peaks and a particular claim may be limited to one peak only, or several peaks. The form APO-IV does not have to include all or even many of the peaks listed in Table 4. Some illustrative and non-limiting possible observations regarding relative intensities of the peaks are set out in Table 4.

TABLE 4

Relative peak intensities for APO-IV

| Angle 2-theta | Relative intensity % |
|---|---|
| 6.84 | 100.00 |
| 9.16 | 79.69 |
| 13.11 | 63.54 |
| 13.87 | 29.61 |
| 15.12 | 18.06 |
| 16.48 | 20.84 |
| 16.74 | 24.92 |
| 17.86 | 93.91 |
| 18.34 | 32.78 |
| 20.92 | 25.95 |
| 21.38 | 26.00 |
| 23.95 | 31.22 |
| 24.60 | 28.09 |
| 25.27 | 58.75 |
| 25.73 | 24.72 |
| 27.05 | 19.81 |
| 28.05 | 25.97 |

Figure 6:
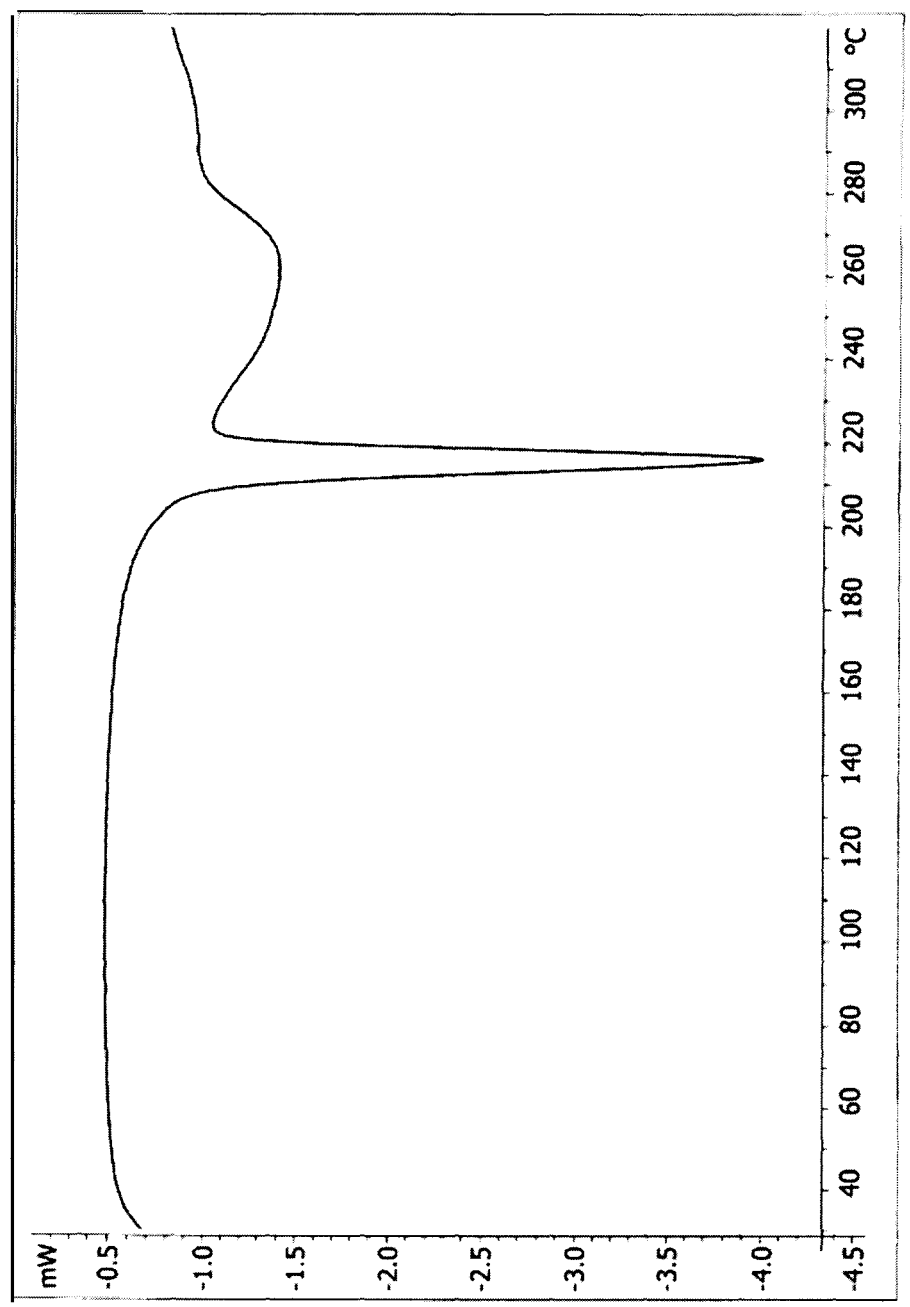
FIG. 6 is a Differential Scanning calorimetry (DSC) thermogram of solid form APO-IV of Nilotinib hydrochloride as prepared in Example 4.

An illustrative DSC thermogram of form APO-IV is shown in FIG. 6. The DSC thermogram shown in FIG. 6 may be illustrative of the type of results obtained when analysing form APO-IV by DSC. The DSC thermogram may be further characterized by a peak endotherm with an onset temperature of approximately 210° C. and a peak maximum of approximately 216° C.

Form APO-IV may be prepared by treating Nilotinib free base with hydrogen chloride in a solvent consisting of isopropanol followed by heating the mixture to a temperature of from about 50° C. to about the boiling point of the solvent. The mixture may be maintained at the elevated temperature for a suitable period of time from a minimum of about 2 hours. Following isolation, form APO-IV may be dried at ambient pressure or in vacuo at a temperature of from about 30° C. to about 60° C. The drying time may vary, depending on the conditions. Often, the minimum drying time is about 12 hours.

In an illustrative embodiment, the present invention comprises a crystalline solid form of Nilotinib hydrochloride which is referred to herein as APO-V. APO-V may be characterized by an X-ray powder diffraction pattern comprising peaks, in terms of degrees 2-theta, at approximately 7.2±0.2, 9.6±0.2, 16.0±0.2, 17.6±0.2, 21.8±0.2 and 26.0±0.2. An illustrative PXRD diffractogram of APO-V is given in FIG. 7.

APO-V may have a reflection ("peak") at any one or more of the values expressed in degrees 2-theta given in Table 5. Although values are given in the tables below, APO-V may be defined by the claimed peaks and a particular claim may be limited to one peak only, or several peaks. The form APO-V does not have to include all or even many of the peaks listed in Table 5. Some illustrative and non-limiting possible observations regarding relative intensities of the peaks are set out in Table 5.

TABLE 5

Relative peak intensities for APO-V

| Angle 2-theta | Relative intensity % |
|---|---|
| 6.19 | 7.18 |
| 7.16 | 26.35 |
| 7.72 | 100.00 |
| 8.59 | 4.70 |
| 9.62 | 14.84 |
| 11.45 | 10.96 |
| 11.64 | 7.75 |

TABLE 5-continued

Relative peak intensities for APO-V

| Angle 2-theta | Relative intensity % |
|---|---|
| 12.42 | 5.73 |
| 14.43 | 5.90 |
| 15.97 | 22.90 |
| 16.34 | 9.01 |
| 17.40 | 16.25 |
| 17.71 | 11.34 |
| 21.82 | 55.83 |
| 22.98 | 24.65 |
| 24.36 | 6.42 |
| 26.00 | 39.36 |
| 28.34 | 14.16 |

Form APO-V may be prepared by further drying form APO-III in vacuo at a minimum temperature of about 50° C. for a period of from about 2 to about 3 days. Often, the vacuum pressure during drying is from about 2 torr to about 4 torr.

EXAMPLES

Powder X-Ray Diffraction (PXRD) Analysis: The data were acquired on a PANalytical X'Pert Pro MPD diffractometer with fixed divergence slits and an X'Celerator RTMS detector. The diffractometer was configured in Bragg-Brentano geometry; data was collected over a 2-theta range of 3-40 using CuKα radiation at a power of 40 mA and 45 kV. CuKβ radiation was removed using a divergent beam nickel filter. The step times shown in Table 6 were used with a step size of 0.017 degrees. Samples were rotated to reduce preferred orientation effects.

TABLE 6

PXRD Parameters

| Form | Holder (mm) | Incident Beam Slits | | Step Time (s) |
|---|---|---|---|---|
| | | Divergent | Anti-scatter | |
| I | 16 | ⅛ | ¼ | 108 |
| II | 27 | ¼ | ½ | 20 |
| III | 16 | ⅛ | ¼ | 108 |
| IV | 16 | ⅛ | ¼ | 54 |
| V | 16 | ⅛ | ¼ | 108 |

Differential Scanning calorimetry (DSC) Analysis: The DSC thermograms were collected on a Mettler-Toledo 821e instrument. Samples (1-5 mg) were weighed into a 40 μL aluminum pan and were crimped closed with an aluminum lid. The samples were analyzed under a flow of nitrogen (ca. 50 mL/min) at a scan rate of 10° C./minute.

Example 1

Preparation of Form APO-I

To a suspension of Nilotinib freebase (5 g) in benzyl alcohol (4 vol) at 20-25° C. was added 20% HCl in IPA (1.0 eq.). A clear solution was obtained after about 10 minutes. The mixture was maintained at 20-25° C. for about 20 hours following precipitation. The suspension was diluted with MTBE (2 vol) and stirred for 10-15 min, filtered and rinsed with MTBE (3×1.5 vol). Following drying in vacuo (40 torr) at 45-50° C. for about 24 hours, form APO-I was obtained. FIG. 1 sets out a PXRD that was obtained from material prepared by this preparation.

Example 2

Preparation of Form APO-II

Figure 2:
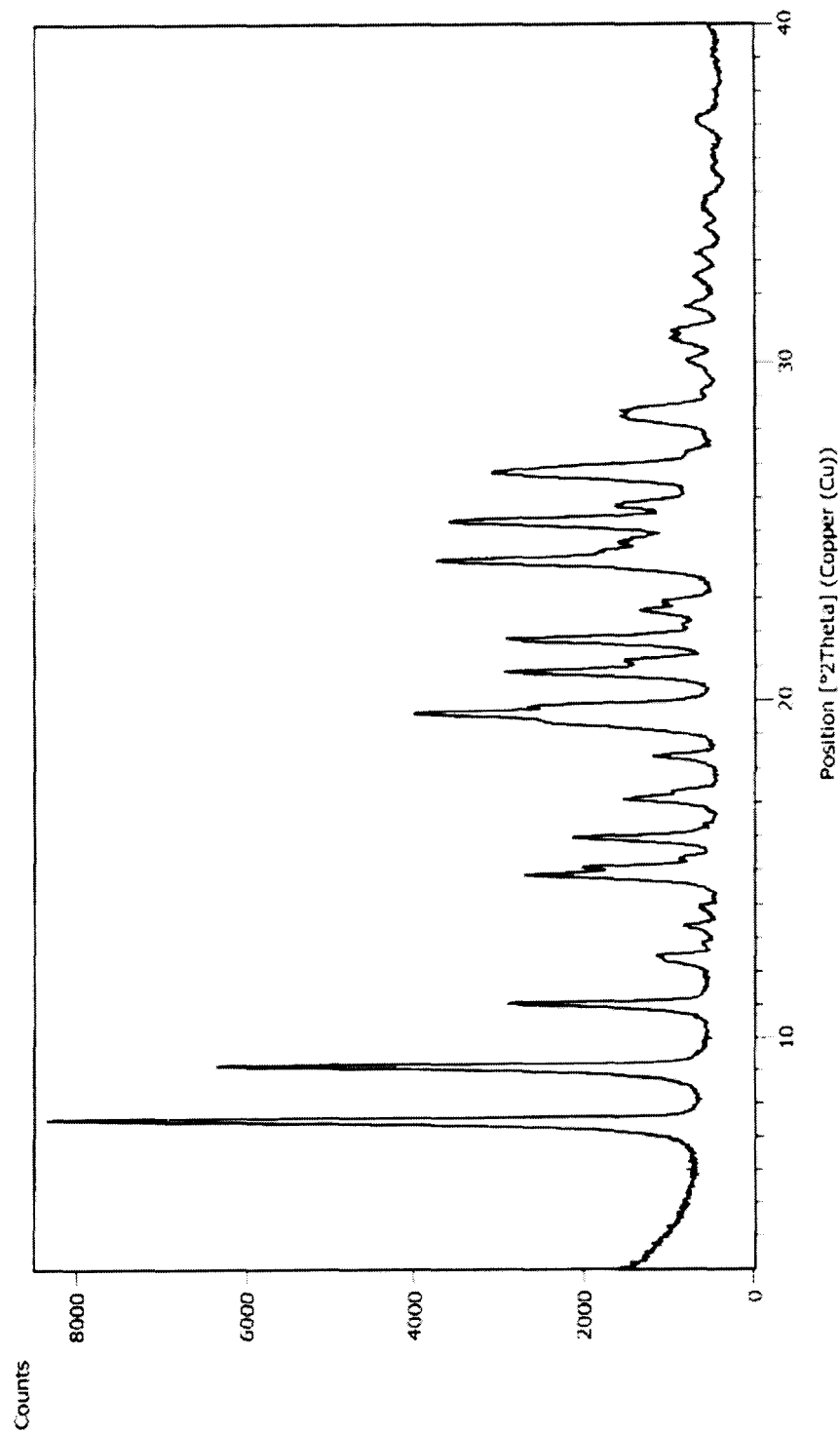
FIG. 2 is a Powder X-Ray Diffractogram (PXRD) of solid form APO-II of Nilotinib hydrochloride as prepared in Example 2.

A suspension of Nilotinib freebase (5.3 g) and 1,2-propanediol (PG) (2.1 eq.) in methanol (5 vol) was warmed to 20-25° C. followed by addition of 20% HCl in IPA (1.0 eq). The suspension nearly dissolved then thickened within a few minutes. The suspension was allowed to stir at 20-25° C. under nitrogen for about 22 hours followed by gradual removal of the methanol at 20-25° C. by rotary evaporation. The remaining solid was further dried in vacuo at 20-25° C. for about 7 hours (35-40 torr) and at 40-45° C. for about 18 hours to yield form APO-II in 100% yield. FIGS. 2 and 3 set out a PXRD and a DSC, respectively, that were obtained from material prepared by this preparation.

Example 3

Preparation of Form APO-III

Figure 4:
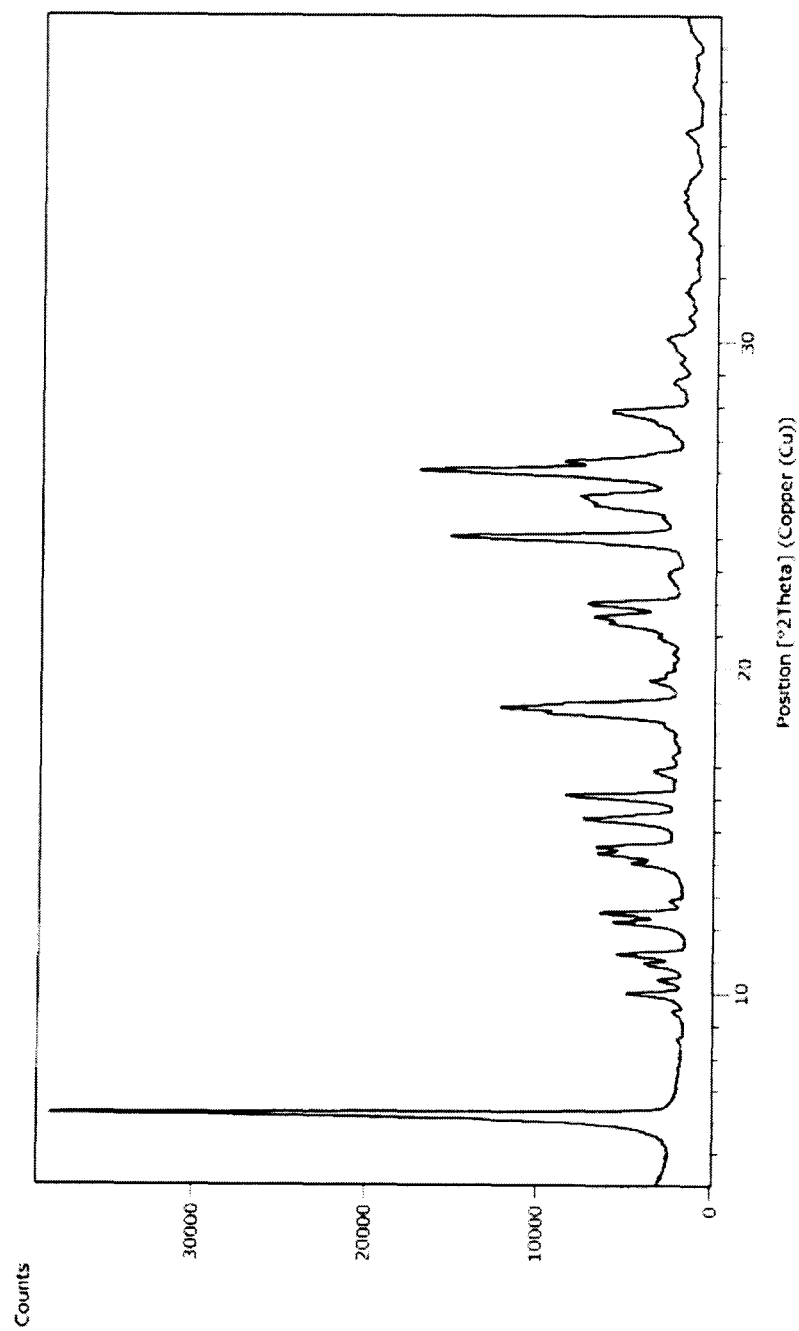
FIG. 4 is a Powder X-Ray Diffractogram (PXRD) of solid form APO-III of Nilotinib hydrochloride as prepared in Example 3.

A suspension of Nilotinib freebase (5.3 g) in glacial acetic acid (4 vol) was warmed to 40-45° C. and stirred until dissolution. To the solution was charged 20% HCl in IPA (1 eq.) at 35-40° C. A precipitate began to form within about 40 minutes. The mixture was allowed to stir at 40-45° C. for about 18 hours. The suspension was then cooled to 25-30° C., filtered and the filter cake was rinsed with methanol (2×1 vol). Following drying under vacuum at 50-55° C. for several hours, form APO-III was obtained (5.4 g). FIG. 4 sets out a PXRD that was obtained from material prepared by this preparation.

Example 4

Preparation of Form APO-IV

Figure 5:
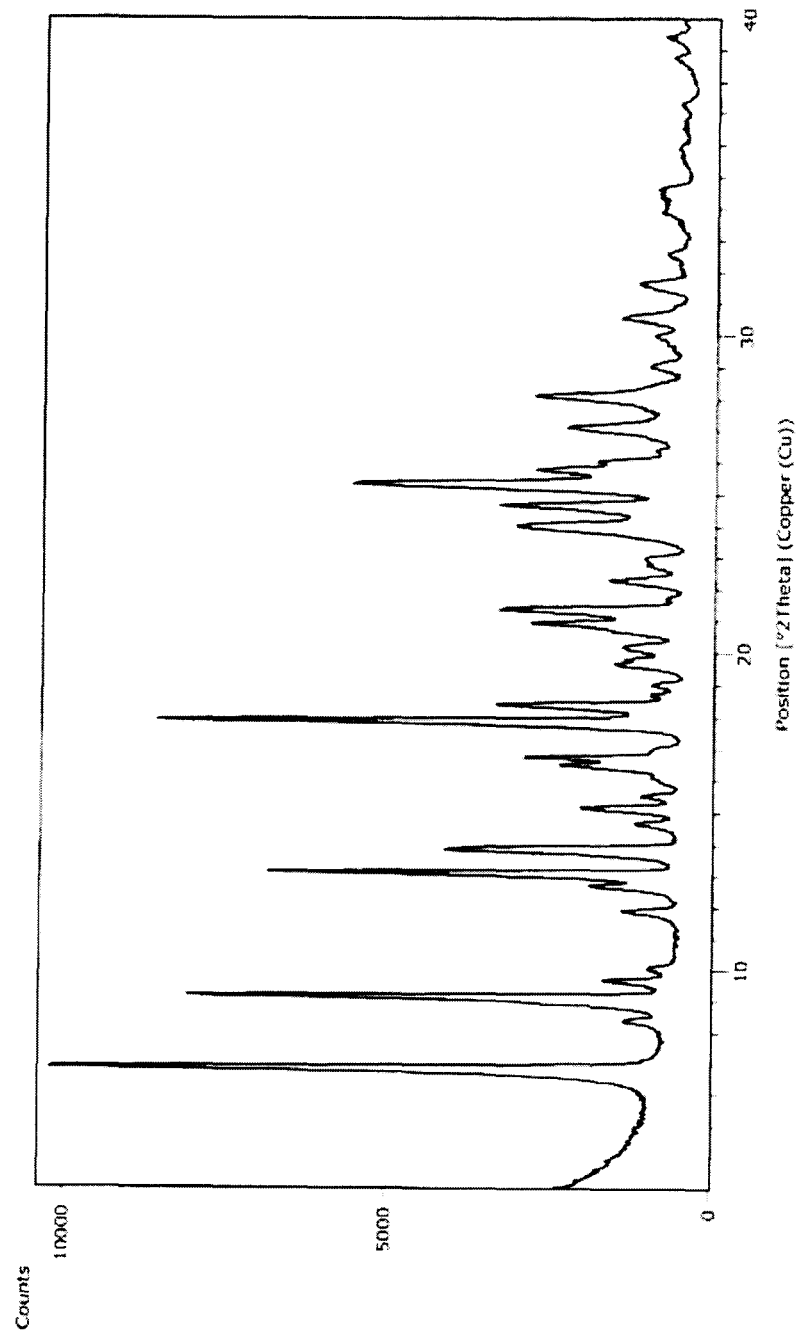
FIG. 5 is a Powder X-Ray Diffractogram (PXRD) of solid form APO-IV of Nilotinib hydrochloride as prepared in Example 4.

To a mechanically stirred suspension of Nilotinib free base (3 g) in isopropanol (22.5 mL) at 20-25° C. under nitrogen, a 20% w/w solution of HCl/IPA (1.03 g) was added dropwise within about 5 minutes, followed by an isopropanol rinse (1.5 mL). The suspension was stirred at 20-25° C. for 1-1.5 hours followed by heating to 80-82° C. for 3-3.5 hours. The suspension was subsequently cooled down to 20-25° C., filtered under a nitrogen stream, washed with isopropanol (2×6 mL) and the product dried in vacuo at 45-50° C. for about 24 hours to yield form APO-IV (3.0 g) as a powder. FIGS. 5 and 6 set out a PXRD and a DSC, respectively, that were obtained from material prepared by this preparation.

Example 5

Preparation of Form APO-V

Figure 7:
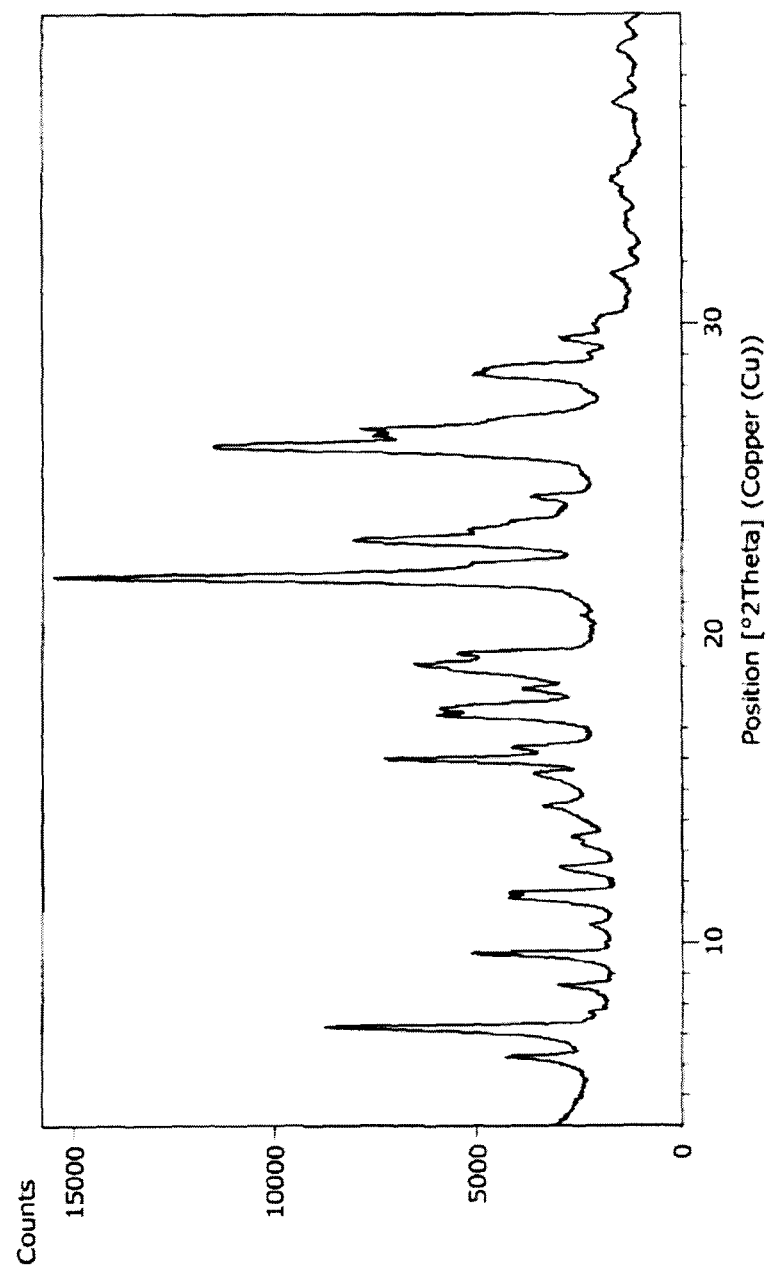
FIG. 7 is a Powder X-Ray Diffractogram (PXRD) of solid form APO-V of Nilotinib hydrochloride as prepared in Example 5.

A sample of APO-III as obtained in Example 3 was dried further in vacuo (2-4 Torr) at 50-55° C. for about 64 hours to yield form APO-V. FIG. 7 sets out a PXRD that was obtained from material prepared by this preparation.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A crystalline solid form of Nilotinib hydrochloride having an X-ray powder diffraction pattern comprising peaks, in terms of degrees 2 -theta, at approximately 6.0, 6.5, 18.1, 19.5, 20.8 and 25.3.

2. The crystalline solid form of Nilotinib hydrochloride of claim 1 having an X-ray powder diffraction pattern as shown in FIG. 1.

3. The crystalline solid form of Nilotinib hydrochloride of claim 1 wherein the crystalline solid form of Nilotinib hydrochloride is a benzyl alcohol solvate wherein the molar ratio of Nilotinib hydrochloride to benzyl alcohol is approximately 1:1.

4. A crystalline solid form of Nilotinib hydrochloride having an X-ray powder diffraction pattern comprising peaks, in terms of degrees 2 -theta, at approximately 7.5, 9.1, 11.0, 19.6, 20.8, 21.8, and 24.1.

5. The crystalline solid form of Nilotinib hydrochloride of claim 4 having an X-ray powder diffraction pattern as shown in FIG. 2.

6. The crystalline solid form of Nilotinib hydrochloride of claim 4 having a differential scanning calorimetry thermogram comprising an endothermic peak with an onset temperature of approximately 134° C.

7. The crystalline solid form of Nilotinib hydrochloride of claim 4 having a differential scanning calorimetry thermogram as shown in FIG. 3.

8. The crystalline solid form of Nilotinib hydrochloride of claim 4 wherein the crystalline solid form of Nilotinib hydrochloride is a propylene glycol solvate wherein the molar ratio of propylene glycol to Nilotinib hydrochloride is approximately 1:1.

9. A crystalline solid form of Nilotinib hydrochloride having an X-ray powder diffraction pattern comprising peaks, in terms of degrees 2 -theta, at approximately 6.2, 12.5, 18.8, 22.0, 24.0, and 26.0.

10. The crystalline solid form of Nilotinib hydrochloride of claim 9 having an X-ray powder diffraction pattern as shown in FIG. 4.

11. The crystalline solid form of Nilotinib hydrochloride of claim 9 wherein crystalline solid form of Nilotinib hydrochloride comprises acetic acid salt wherein the molar ratio of acetic acid to Nilotinib hydrochloride is approximately 2:1.

12. A crystalline solid form of Nilotinib hydrochloride having an X-ray powder diffraction pattern comprising peaks, in terms of degrees 2 -theta, at approximately 6.8, 9.2, 13.1, 13.9, 17.9 and 25.3.

13. The crystalline solid form of Nilotinib hydrochloride of claim 12 having an X-ray powder diffraction pattern as shown in FIG. 5.

14. The crystalline solid form of Nilotinib hydrochloride of claim 12 having a differential scanning calorimetry thermogram comprising an endothermic peak with an onset temperature of approximately 210° C.

15. The crystalline solid form of Nilotinib hydrochloride of claim 12 having a differential scanning calorimetry thermogram as shown in FIG. 6.

16. A crystalline solid form of Nilotinib hydrochloride having an X-ray powder diffraction pattern comprising peaks, in terms of degrees 2 -theta, at approximately 7.2, 9.6, 16.0, 17.6, 21.8, and 26.0.

17. The crystalline solid form of Nilotinib hydrochloride of claim 16 having an X-ray powder diffraction pattern as shown in FIG. 7.

18. The crystalline solid form of Nilotinib hydrochloride of claim 16 wherein the crystalline solid form of Nilotinib hydrochloride comprises acetic acid salt wherein the molar ratio of acetic acid to Nilotinib hydrochloride is approximately 1:1.

* * * * *